United States Patent [19]
Pallikaris

[11] Patent Number: 5,699,810
[45] Date of Patent: Dec. 23, 1997

[54] PROCEDURE FOR REMOVAL OF SOFT EYE TISSUE

[76] Inventor: Ioannis G. Pallikaris, c/o University of Crete Medical School, Department of Opthalmology P.O. Box 1352, Heraklion Crete 711 10, Greece

[21] Appl. No.: 339,243

[22] Filed: Nov. 10, 1994

[51] Int. Cl.$^6$ .................................................. A61B 17/00
[52] U.S. Cl. .................................................. 128/898
[58] Field of Search ..................... 128/897, 898; 604/22, 49, 289, 294, 296; 606/166, 161, 162; 433/25, 166, 216

[56] References Cited

U.S. PATENT DOCUMENTS

| | | |
|---|---|---|
| D. 340,807 | 11/1993 | Fertal . |
| 1,624,758 | 4/1927 | Powell et al. . |
| 2,137,286 | 11/1938 | Herbig . |
| 2,630,114 | 3/1953 | Hart . |
| 2,742,936 | 4/1956 | Cooley . |
| 3,106,732 | 10/1963 | Dayton et al. . |
| 3,757,419 | 9/1973 | Hopkins . |
| 3,986,272 | 10/1976 | Feierabent . |
| 4,137,588 | 2/1979 | Sandt et al. . |
| 4,173,980 | 11/1979 | Curtin . |
| 4,320,761 | 3/1982 | Haddad . |
| 4,378,804 | 4/1983 | Cortese, Jr. . |
| 4,739,532 | 4/1988 | Behrend . |
| 4,759,240 | 7/1988 | Lin . |
| 4,869,277 | 9/1989 | Olsen ........................ 433/166 |
| 5,235,716 | 8/1993 | Stella . |
| 5,273,559 | 12/1993 | Hammer et al. ............ 433/166 |
| 5,312,330 | 5/1994 | Klopotek ................... 606/166 |
| 5,395,385 | 3/1995 | Kilmer et al. .............. 606/166 |

FOREIGN PATENT DOCUMENTS

| | | | |
|---|---|---|---|
| 4243219 | 6/1994 | Germany .................. | 433/216 |
| WO 93/22988 | 11/1993 | WIPO . | |

OTHER PUBLICATIONS

Pallikaris IG, Karoutis AD, Lydataki SE, Siganos DS. Rotating Brush for Fast Removal of Corneal Epithelium, J. Refract. Corneal Surg., Jul./Aug. 1994;10:439–442.

Dausch D, Klein FJ, Shroeder E. Opthalmic Excimer Laser Surgery. Editions du Signe Publications, Strasbourg; 1991:97.

Taylor DM, L'Esperance FA, Del Pero RA, et al. Human Excimer Laser Lammellar Keratectomy; A Clinical Study. Opthalmology. 1989;96:654–664.

Taylor DM, L'Esperance FA, Warner JW, et al. Experimental Corneal Studies With The Excimer Laser. J Cataract Refract Surg. 1989;15:384–389.

Zabel RW, Sher NA, Ostrov CS, Parker P, Lindstrom RL. Myopic Excimer Laser Keratectomy: A Preliminary Report. J. Refract Corneal Surg. 1990;6:329–334.

Eiferman RA, O'Neil KP, Forgey DR, Cook YD. Excimer Laser Photorefractive Keratectomy for Myopia: Six–Month Results. J. Refract Corneal Surg. 1991;7:344–347.

(List continued on next page.)

*Primary Examiner*—Angela D. Sykes
*Assistant Examiner*—Samuel Gilbert

[57] ABSTRACT

A surgical procedure and device are used to precisely remove soft tissue from the eye. For example, a corneal epithelial layer is removed from the eye as part of a photorefractive keratectomy (PRK) or phototherapeutic keratectomy (PTK) procedure. In the procedure, the epithelial layer is abraded, under irrigation, using a relatively soft and pliable rotating abrading surface. The device used to perform the procedure is a hand-held rotary brush having semi-rigid plastic bristles with flat polished ends. In another embodiment, a rotating abrading surface is provided by open cells of a sponge material, instead of a brush. In this manner, the epithelium can be abraded away within a few seconds in a precisely defined area without causing mechanical damage to the underlying stromal layer. In a further application, the tool is used to remove a so-called pseudo-membrane formed during laser ablation of the corneal stroma during PRK or PTK.

19 Claims, 4 Drawing Sheets

OTHER PUBLICATIONS

Seiler T, Kahle G, Kriegerowski M. Excimer Laser (193nm) Myopic Keratomileusis in Sighted and Blind Human Eyes. J. Refract Corneal Surg. 1990;6:165–173.

Maguire LJ, Zabel RW, Parker P, Lindstrom RL. Topography and Ray Tracing Analysis of Patients With Excellent Visual Acuity 3 Months After Excimer Laser Photorefractive Keratectomy for Myopia. Refract Corneal Sur. 1991;7:122–128.

McDonnel PJ, Garbus JJ, Salz JJ. Excimer Laser Myopic Photorefractive Keratectomy After Radial Keratectomy. Refract Corneal Surg. 191;7:146–150.

Mouillon M, Romanet JP. Epithelium et chirurgic refractive II. Photokeratectomie. In. D. Rigal, ed., L'epithelium corneen, Masson Publications, Paris. 1993;634.

Seiler T, Bende T, Wollensak J, Trokel S. Excimer Laser Keratectomy for Correction of Astigmatism. Am J Opthalmol. 1988;105:117–124.

Seiler T, Kreigerowski M, Schnoy N, Bende T. Ablation Rate Of Human Corneal Epithelium and Bowman's Layer With Excimer Laser (193nm). Refract Corneal Surg. 1990;6:99–102.

Rigal D, Fonction Optique. In. D.Rigal, ed., L'epithelium corneen, Masson Publications, Paris; 1993;64–69.

Simon G, Ren Q, Kervick GN, Parel JM. Optics of the Cornea Epithelium. Refract Corneal Surg. 1993;9:42–50.

Simon G, Parel JM, Kervick G, Rol P, Thompson K. Corneal Epithelium, Visual Acuity, and Laser Refractive Keratectomy. Opthalmic Technologies. 1991;1423:154–156.

Alio JL, Ismael MM, Artola, A. Laser Epithelium Removal Before Photorefractive Keratectomy. Refract Corneal Surg. 1993:9(5):395.

Dafton H. *Physiology of the Eye*. Pergamon Press Inc. Chapter 3: The Cornea. 5:105–138 (1990).

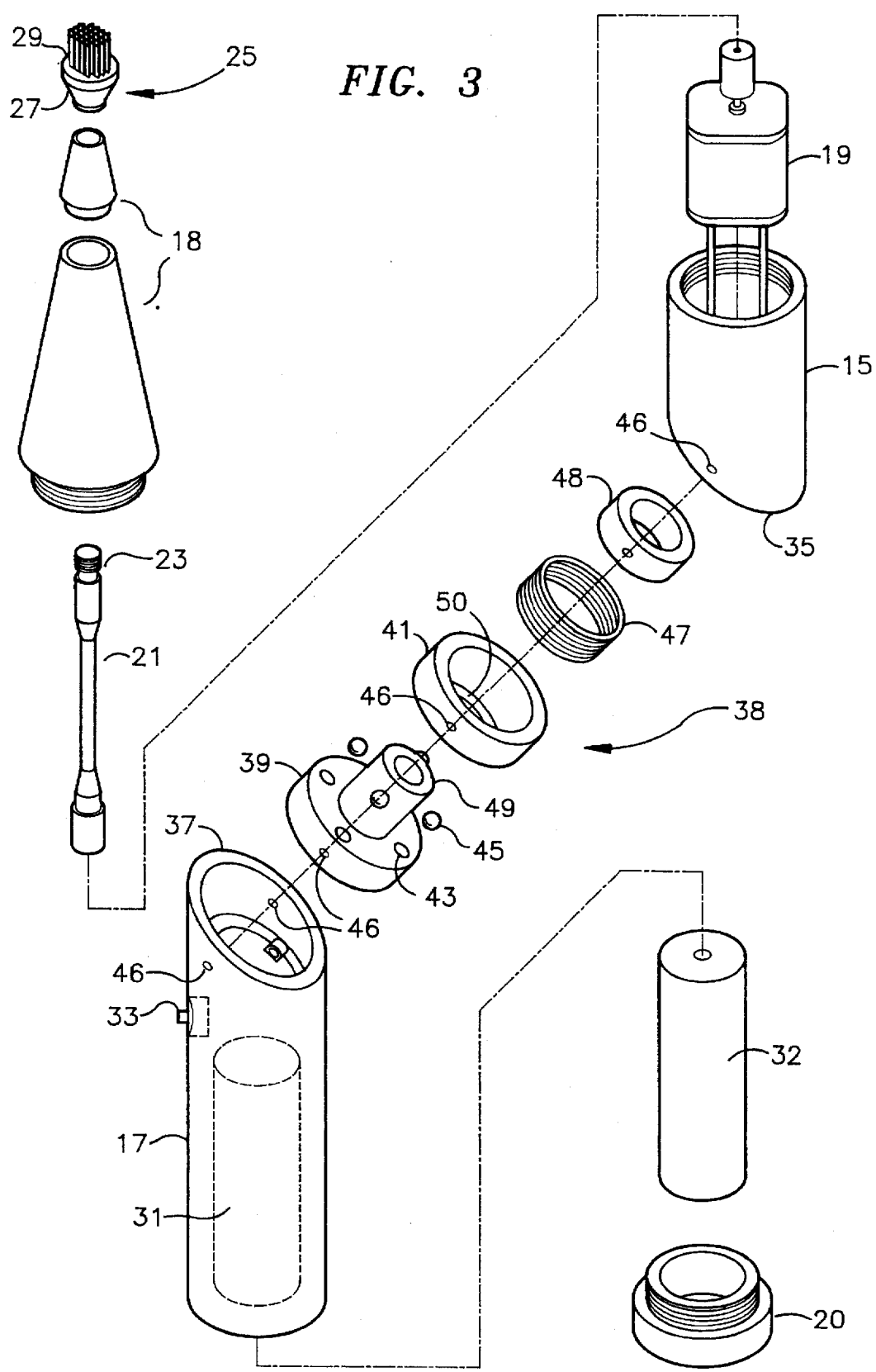

PROCEDURE FOR REMOVAL OF SOFT EYE TISSUE

BACKGROUND OF THE INVENTION

The present invention relates to eye surgery. In particular, the invention concerns procedures and devices used to mechanically remove eye tissue, e.g., to remove an epithelial layer of the cornea as a preliminary step in a laser-based corneal reshaping procedure. Such procedures include photorefractive keratectomy (IRK) used to surgically correct refractive errors, and phototherapeutic keratectomy (PTK) used to remove corneal abnormalities such as scar tissue.

As illustrated in FIG. 1, the great bull of the cornea of the eye is made up of the stroma 1 (up to 90% of its thickness). The stroma 1 is bounded externally by Bowman's membrane 3 and the epithelium 5. Internally, the stroma 1 is bounded by Descemet's membrane 7 and the endothelium 9. The total thickness of the cornea in man is just over 0.5 mm in the central region, and towards the periphery it becomes some 50% thicker.

The epithelium 5 is a highly organized soft cellular structure consisting of some five or six layers of regenerative cells with a total thickness of 50 to 100 µm. The coils at the base 11 are columnar, but as they are squeezed forward by the generation of new cells, they become flatter as shown at 13.

In contrast, Bowman's membrane 3 (the outermost layer of the stroma) is much less ordered, consisting of collagen fibrils closely but randomly packed into a felt-like layer which is not sharply differentiated from the remainder of the stroma beneath it. Due to its fibrous structure, the stroma is substantially firmer and more cohesive than the epithelium.

In the known PRK and PTK techniques, ablation of the cornea is effected by impingement of laser pulses (produced, e.g., by a 193 nm excimer laser) onto the stroma 1 in a highly controlled manner under a surgical microscope. In PRK, the desired degree of ablation across the cornea is determined by comparing the actual corneal shape to the desired ideal cornea/shape. Then, the number of ablating laser pulses is computed from the desired degree of ablation and the known ablation rate of the stroma.

Before the stroma can be ablated, the overlying epithelial layer must be removed. The cornea/epithelium can be removed by means of the laser used to ablate the stroma. Such removal is very rapid, and the underlying stromal surface can be of very good quality. However, this procedure has significant drawbacks. Owing to their respective different structures, the ablation rate of the corneal epithelium is faster ($0.68\pm0.151$ µm/pulse) than that of the corneal stroma ($0.55\pm0.1$ µm/pulse). Moreover, unlike the stroma, the ablation rate of the corneal epithelium is quite non-homogeneous, and it is clinically impossible to quantify exactly the depth of the epithelium to be ablated for every eye. These factors make very difficult calculation of the required number of laser pulses to first remove the epithelial layer and then achieve the desired ablation of the stroma.

Another known approach for removing the corneal epithelial layer is by softening the layer with chemicals such as alcohol or cocaine, and wiping the softened layer away with a filter paper. This approach has a serious drawback in that the chemicals react with the underlying stromal layer causing changes which can adversely affect the following laser ablation procedure.

Accordingly, the conventional PRK and PTK procedures most typically involve an initial removal of the epithelium using mechanical means. Once the epithelium is mechanically removed, laser pulses are used to precisely ablate (and, in the case of PRK, thereby reshape) the underlying stroma.

Conventionally, the corneal epithelium is removed by scraping the same with a surgical knife (e.g., a beaver or hockey knife). In such a procedure, the cells of the epithelium are first broken up and then swept away. However, even with the exercise of great skill and care, it is difficult with this technique to avoid the formation of surface irregularities (e.g., nicks and cuts) on the underlying stroma. It is also difficult to ensure that all of the epithelial cells are removed from the desired area. In the following stromal photoablation, the irregularities of the stromal surface are susceptible to reproduction in the final remodeled surface. Moreover, bearing in mind the differences in the optical properties and ablation rate between the epithelium and stroma, the remodeled surface can be made even more irregular when residual epithelial cells remain. Such irregularity may lead to a degradation of the optical quality of the remodeled surface, and diminishes the accurate reproducibility of the procedure.

Another disadvantage of the existing methods for removal of the corneal epithelium, especially the mechanical and laser methods, is that they take at least several minutes to perform. During this time, the cornea can dehydrate. This can adversely affect the following laser ablation of the stroma in a PRK or PTK procedure.

Curtin U.S. Pat. No. 4,173,980 discloses a rotary grinding lap or disk and an associated procedure for resurfacing a cornea. The device is large and complicated. Moreover, the disclosed procedure and tool are designed to mechanically reshape the entire cornea in order to correct vision defects, not to perform a selective removal of soft tissue such as a corneal epithelial layer.

Haddad U.S. Pat. No. 4,320,761 discloses a procedure and hand-held surgical device for excision of eye tissue such as cataracts. No disclosure is provided that the tool may be used for the selective removal of only a corneal epithelium. Additionally, since the device employs a rotary cutting stylus, if it were used to remove a cornea/epithelium it would be prone to causing picks and cuts in the underlying stroma, like the conventional scraping technique.

Hand-held rotary brushes and scrubbing devices for the treatment and/or cleaning of human body parts (e.g. the skin and teeth) are known. See, e.g., Cortese, Jr. U.S. Pat. No. 4,378,804; Behrend U.S. Pat. No. 4,739,532; Dayton et at. U.S. Pat. No. 3,106,732; and Hopkins U.S. Pat. No. 3,757,419. None of these devices is particularly suited for the precise selective removal of soft eye tissue, e.g., a corneal epithelial layer.

SUMMARY OF THE INVENTION

In view of the above, it is an object of the invention to provide a procedure and device which are particularly suited for the selective removal of soft eye tissue, and which minimize the chance of causing damage to surrounding tissue.

It is a more particular object of the invention to provide a procedure and device for removal of a corneal epithelial layer with improved precision, i.e., providing complete removal of the epithelial cells within a desired area (no residual cell material) and no damage to the underlying stromal layer.

It is another object of the invention to provide a procedure and device which drastically reduce the time required to remove a corneal epithelial layer.

Yet another object of the present invention is to provide an improved technique for removal of a corneal epithelial layer as part of a corneal laser ablation (e.g., PRK and PTK) procedure.

Another specific object of the invention is to provide a procedure and device useful for removing a so-called pseudo-membrane created by the laser ablation of PRK or PTK procedures.

These and other objects are achieved by the various aspects of the present invention summarized below.

In a first aspect of the invention, a procedure for removing a corneal epithelial layer from an eye includes the following steps. A corneal surface of the eye is exposed. A relatively soft and pliable abrading surface is rotated about a tool axis. The rotating abrading surface is then applied to the corneal surface for a sufficient time to abrade away a corneal epithelial layer, while leaving an underlying stromal layer wholly intact. This procedure may be performed as part of a corneal laser ablation procedure (such as PRK or PTK), including the subsequent step of ablating the underlying stromal layer in a controlled manner by impinging a laser beam thereon.

In a second aspect of the invention, a procedure for removing soft tissue from an eye comprises the steps of exposing a soft tissue of the eye, rotating a relatively soft and pliable abrading surface about a tool axis, and applying the rotating abrading surface to the soft tissue for a sufficient time to abrade away the same.

A third aspect of the present invention is embodied in a surgical device for removing eye tissue. The device has a housing and a motor disposed within the housing. A shaft is rotatably coupled to the motor. The shaft defines a rotation axis and has an end extending from the housing. An abrading head is mounted on the end of the shaft. The head comprises a relatively soft and pliable abrading surface rotatable about the rotation axis through a circular swath having a diameter of 4–10 min. In one embodiment, the pliable abrading surface is provided by a brush having semi-rigid plastic bristles. In another embodiment, the pliable abrading surface is provided by the open-cells of a sponge-material.

The above and other objects, features and advantages of the present invention will be apparent and fully understood from the following detailed description of the preferred embodiments, taken in connection with the appended drawings.

BRIEF DESCRIPTION OF THE DRAWINGS

FIG. 3 is an exploded perspective view illustrating the individual parts of the tool shown in FIG. 1.

DETAILED DESCRIPTION OF THE PREFERRED EMBODIMENTS

The procedures of the present invention involve generally the selective removal of soft eye tissue without causing damage to surrounding tissues, by abrading away the soft eye tissue with a relatively soft and pliable rotating abrading surface. In a first embodiment of the invention, the rotating abrading surface is used to abrade away a corneal epithelial layer, while leaving the underlying stroma wholly intact. A further application of the invention is in the removal of a so-called pseudo-membrane formed by laser ablation in a PRK or PTK procedure. Exemplary tools for use in the inventive procedures are described below. Thereafter, the procedures are described in greater detail in connection with comparative test results illustrating the advantages of the inventive methods over conventional techniques.

Figures 2, 4, 5:
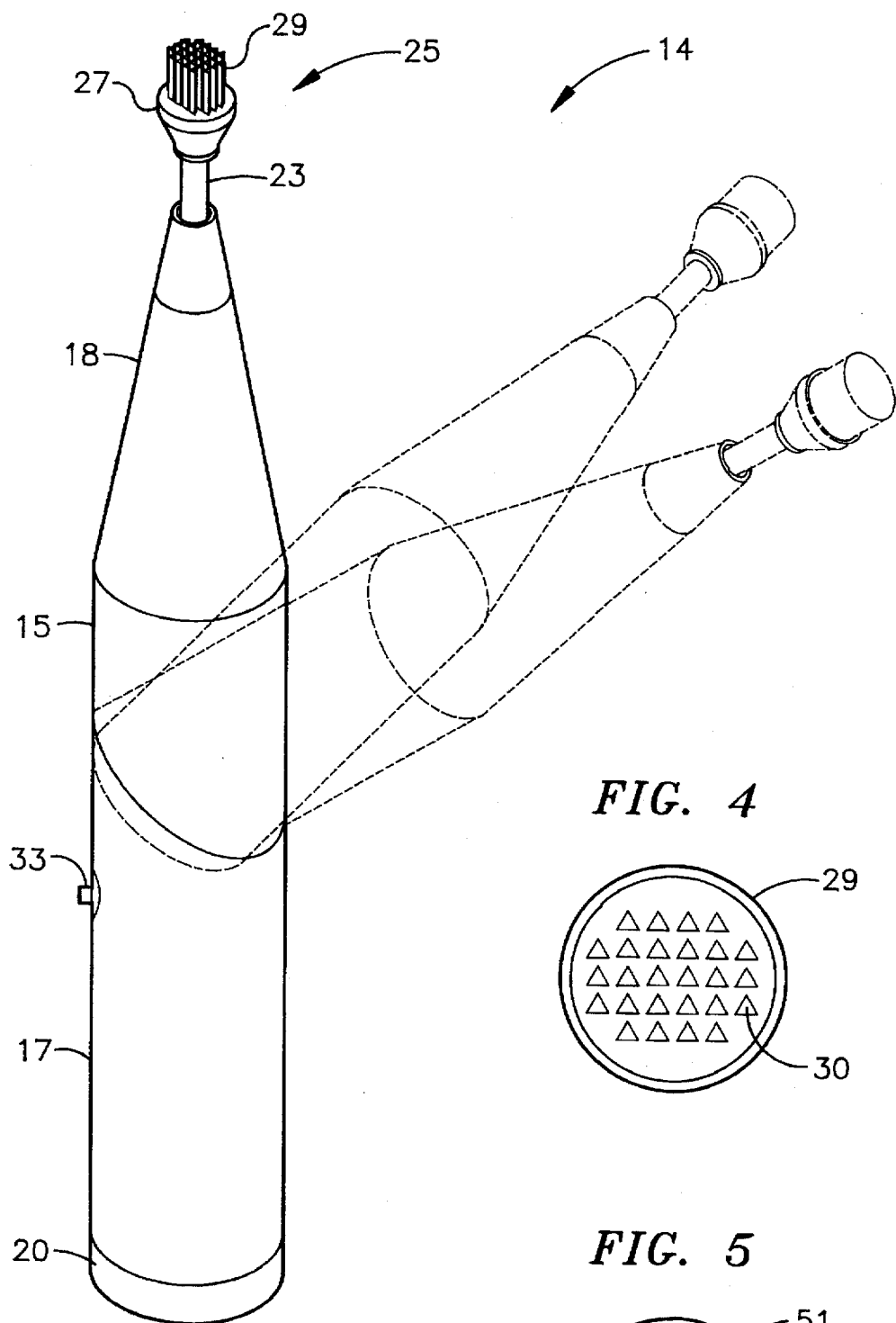
FIG. 2 is a perspective view of a hand-held rotating brush device in accordance with the invention.
FIG. 4 is a top plan view of the rotating brush included in the tool shown in FIGS. 2 and 3.
FIG. 5 is a top plan view illustrating an alternative embodiment of the invention wherein a sponge material is substituted for the rotating brush.

Referring to FIGS. 2 and 3, illustrated is a hand-held rotary device 14 for removal of eye tissue in accordance with the present invention. Device 14 comprises a tubular housing having forward and rearward cylindrical segments 15, 17, a conical nose cone assembly 18 threadedly received in a forward end of segment 15, and an end cap 20 threadedly received in a rearward end of segment 17. Disposed within forward segment 15 is an electric motor 19. A shaft 21 is rotably coupled to motor 19. Shaft 21 defines a rotation axis of the tool and has an end 23 extending from nose cone 18. Shaft end 23 is threaded to receive thereon an abrading head 25 comprising a cup 27 for receiving an insert providing a relatively soft and pliable abrading surface. In the first illustrated embodiment, the abrading surface is provided by a circular brush 29 (to be described in detail hereinafter).

Electric motor 19 should provide a rotation speed of between 4000–6000 rpm, with 5000 rpm being preferred. A suitable small DC commutator motor operable at 1.5 V is manufactured by Gebr. Buhler Nachtolger GmbH, D-8500 Nurnberg 45. Shaft 21, as shown, is straight and rigid, being made of surgical steel or the like. Alternatively, a flexible shaft (e.g., a torsion cable as shown in Hopkins U.S. Pat. No. 3,757,419) could be used to rotate brush 29 at an angle with respect to the spin axis of the motor.

Rearward segment 17 forms a compartment 31 for housing a 1.5 V size AA battery 32. Battery 32 is connected to motor 19 through a circuit comprising a simple spring-biased on-off switch 33 and contacts (not shown) at opposite ends of battery compartment 32. End cap 20 can be unscrewed from the rearward end of segment 17 to allow access to battery compartment 32.

Instead of a simple on-off switch, a work-actuated switch could be used, such as is disclosed in Dayton et at. U.S. Pat. No. 3,106,732. Such a switch could serve simply to provide added convenience by turning the motor on when the brush contacts the eye and/or as a safety feature by turning the motor off in the event excess pressure is applied against the eye.

In the preferred illustrated embodiment, forward segment 15 and rearward segment 17 are pivotal with respect to each other on an oblique plane formed by their respective mating end surfaces 35, 37. By pivoting the housing segments, an angled handle shape can readily be provided. A spring-biased detent mechanism 38 allows the handle segments to be rotated between four positions (see FIG. 3—three positions shown) in order to provide the handle shape which is most comfortable for the surgeon. Detent mechanism 38 comprises annular bushing members 39 and 41, each having equi-spaced conical recesses 43. Recesses 43 form seats for ball bearings 45. Bushings 39 and 41 are mated to each other and rotated to bring respective pairs of recesses into registration with each other, thus defining the different handle positions. Bushings 39 and 41 are secured, respectively, inside the mating ends of segments 15 and 17, such as by screws passing through holes 46. Bushing 41 is held in a tight resilient engagement with bushing 39 by a compression spring 47. Spring 47 is disposed between a ring flange 48 secured by a set screw to a small diameter portion 49 of bushing 39, and an inner annular ledge 50 of bushing 41.

Other potentially suitable pivotal handle arrangements are disclosed in Hart U.S. Pat. No. 2,630,114; Lin U.S. Pat. No. 4,759,240; and Cooley U.S. Pat. No. 2,742,936.

Brush 29 is formed of semi-rigid plastic bristles 30. It is critical that the plastic bristles be formed such that when rotated they easily break-up and completely remove the cells of the corneal epithelium, without doing damage to the underlying Bowman's membrane. The former requires that the bristles be rigid enough so that they do not simply collapse or bend completely over when rotated and applied against the corneal epithelium. The latter requires that the bristles be soft and pliable enough such that scratching or cutting of the underlying stroma can be easily avoided. The inventor has found that the type of bristles commonly employed in surgical scrub brushes can be adapted to meet the necessary criteria. In particular, the source material for the bristles can be a plastic surgical hand brush (903 brosse chirurgicale, Laboratoires Pharmaceutiques VYGON— Ecouen, France). Such a brush has a rectangular base (5 cm by 8.3 cm) formed of PVC, from which relatively soft and pliable bristles of the same material emerge, each being about 1.2 cm in length and having an average thickness of about 0.7 min. The bristles have a triangular cross-sectional shape (best seen in FIG. 4) which tapers slightly from the base to the ends. Due to the taper, the bristles are stiffer toward the base of the brush and more flexible toward the ends. Thus, by cutting the bristles to different lengths, the stiffness of the bristles can be adjusted.

In a simple technique for manufacturing the device, small cylindrical pieces having a cross-sectional diameter corresponding to the site of the area to be treated are carefully cut from the brush. Generally, the diameter should fall within the range of 4–10 mm, with 7 mm being suitable for most applications, in order to provide a correspondingly sized circular rotation swath. These dimensions correspond to the range of diameters of the human cornea areas which are normally treated in a corneal laser ablation procedure such as PRK or PTK.) The cylindrical pieces are then secured in cup 27, such as by a suitable adhesive. The cylindrical pieces could also be removably secured in the cup 27 so that they could be easily replaced as necessary, e.g., due to damage or contamination.

After having tested some brush pieces of different bristle lengths on rabbit corneas, it was determined that an appropriate bristle length is 5 mm. However, particularly when larger diameters such as 8 and 10 mm are used, it is desirable to provide the bristles of varying length so as to form a spherically concave abrading surface generally following the curve of the cornea. The ends of the bristles should be polished flat and smooth. This can be done by fixing a very fine sand paper to a smooth hard surface and rotating the brush on it. Finally, the brush obtained should be rinsed in flowing water so that any debris is removed. Further cleaning of the constructed corneal epithelium remover is achieved by letting the brush rotate in distilled water, at the speed offered by the motor. The latter cleaning procedure is recommended prior to each use.

Obviously, in order to mass produce the device, other manufacturing techniques can be utilized to form the brush. For example, instead of cutting out and trimming segments from an existing surgical brush, the segments could be formed in the proper size and configuration by known molding techniques such as injection molding.

In the alternative embodiment illustrated in FIG. 5, a sponge material is substituted for brush 29. The sponge could be natural or synthetic, e.g., plastic. In this case, it is the open cells of sponge material 51 that provide a relatively soft and pliable abrading surface capable of removing a corneal epithelial layer without damaging the underlying stroma. Particularly for large diameters, sponge 51 may be provided with a concave spherical shape generally following the curve of the cornea.

Although not illustrated, it may also be deskable to build into device 13 an irrigation system for keeping the eye tissue moist during the procedure, and for carrying away the abraded tissue. Such a system employing a fluid source and vacuum tube is disclosed in Haddad U.S. Pat. No. 4,320,761.

To use device 14, switch 33 is depressed to turn on motor 19. This in turn causes brush 29 (or sponge 51) to rotate at about 5000 rpm about a longitudinal tool axis defined by the shaft 21. The eye to be treated is maintained in an exposed stationary condition while the rotating brush is lightly applied to the central cornea. In just a few seconds (generally no more than five) the corneal epithelial layer will be cleanly abraded away, while leaving the underlying stromal layer wholly intact.

Procedures in accordance with the invention are further described below in connection with comparative tests that have been performed on rabbit and human subjects. The device used in these tests was a corneal foreign body removal device, manufactured by F. L. Fischer GmbH & Co. Medizin-Technik-Feiburg, Germany, modified in accordance with the invention to include a rotating brush head as described herein.

Animal Electron Microscopy Studies

The corneal epithelium of three rabbits was removed using a beaver blade on one eye and the rotating brush device on the other eye. The beaver blade was used to remove the corneal epithelium of both eyes of a fourth rabbit. The rotating brush device was used to remove the corneal epithelium of both eyes of a fifth rabbit. In all cases, tetracaine hydrochloride 0.5% eye drops (TETRACAINE HYDROCHLORIDE, COOPER S.A.—Athens, Greece) were applied both as a local anesthetic and epithelial softener, one drop every five minutes for a total of three drops immediately prior to removing the epithelium. Immediately after epithelial removal, the animals were sacrificed and all eyes were separately prepared for scanning electron microscopy (SEM) and transmission electron microscopy (TEM).

Figure 6A:
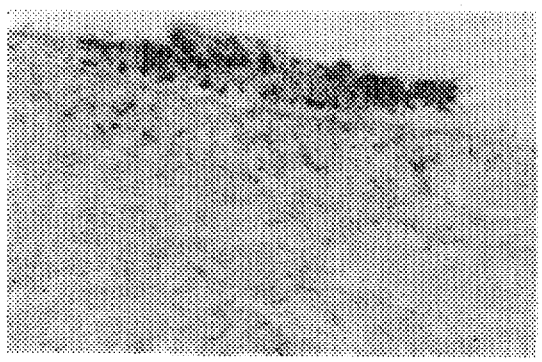
FIGS. 6A, 6B, 7A, 7B are comparative transmission electron microscopy (TEM) and scanning electron microscopy (SEM) photographs of rabbit corneal surfaces following epithelial removal.

Corneal surface abnormalities following the conventional beaver knife epithelial removal technique were clearly seen in almost all cases. FIG. 6A is a TEM photograph of a rabbit corneal surface following epithelial removal by a beaver blade. The epithelium was inadequately removed (remnants are seen). The basement membrane is well distinguished as a darker horizontal line at the upper part of the photographs, above which epithelial cell remnants and hemidesmosomes are also seen.

Figure 7A:

FIG. 7A is a TEM photograph of a rabbit corneal surface, following epithelial removal using the rotating brush device. In contrast to FIG. 6A, the basement membrane almost coincides with the upper top line separating the air and corneal tissue. No epithelial cell remnants above the basement membrane are distinguished. There is also no sign of any damage to the collagen fibers in the underlying stroma.

Figure 6B:
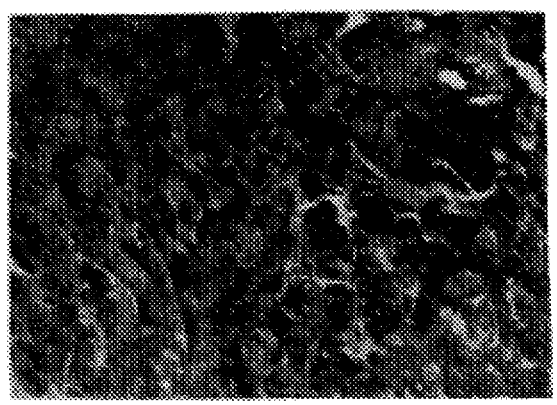
Figure 7B:
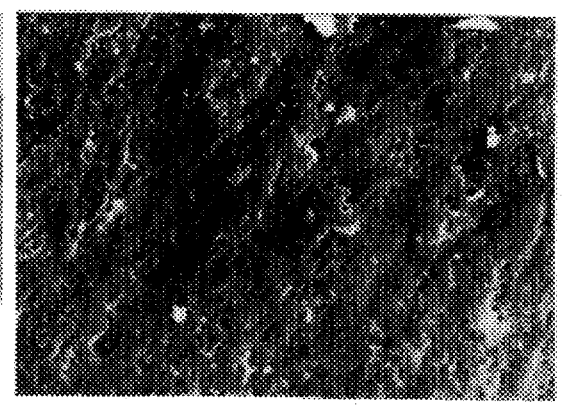

FIGS. 6B and 7B are SEM photographs of the eyes shown in FIGS. 6A and 7B, respectively. FIG. 7B shows a smooth stromal surface following epithelial removal by the rotating brush device. No epithelial cell remnants are seen. This is not the case for the stromal surface of FIG. 6B where the epithelium was removed by the classical method. In this case, epithelial cell remnants are clearly seen. These tests indicate that a much more even and smooth stromal surface is obtained following corneal epithelium removal by means of the rotating brush device.

Human Eye PRK Studies

Pre-PRK epithelial abrasion (removal) time and post-PRK reepithelialization time were evaluated in a series of forty human eyes undergoing PRK for low to moderate myopia. The rotating brush technique was used to remove the cornea/epithelium prior to PRK. Tetracaine eye drops were applied to the eye, one drop every five minutes for a total of three drops prior to removing the epithelium. After inserting a Barraquer lid speculum, the patient was asked to fixate his other eye on the microscope light. The rotating brush was lightly applied to the central cornea for a few seconds (1–3 sec) under continuous irrigation with normal saline. The corneal surface was immediately gently cleaned with a dry micro-sponge, then recleaned with a micro-sponge wetted with normal saline. Next, a standard PRK ablation procedure was performed using an Aesculap Meditec Excimer Laser (MEL 60—Heroldsberg, Germany) producing a beam with a confluence at the cornea of 220 mJ/cm$^2$ per pulse, at a firing rate of 20 Hz. After excimer laser ablation, the ablated bed was irrigated for approximately 5–10 seconds with normal saline. At the end of the surgery, tobramycin sulfate eye ointment (Tobrex—tobramycin 3 mg, ALCON COUVREUR NV—SA, Belgium) was applied on the eye and the eye was pressure-patched. The entire procedure was performed under the surgical microscope of the excimer laser unit. The eye patch was changed every 24 hours until re-epithelialization was complete, at which time the patch was removed.

Figure 1:
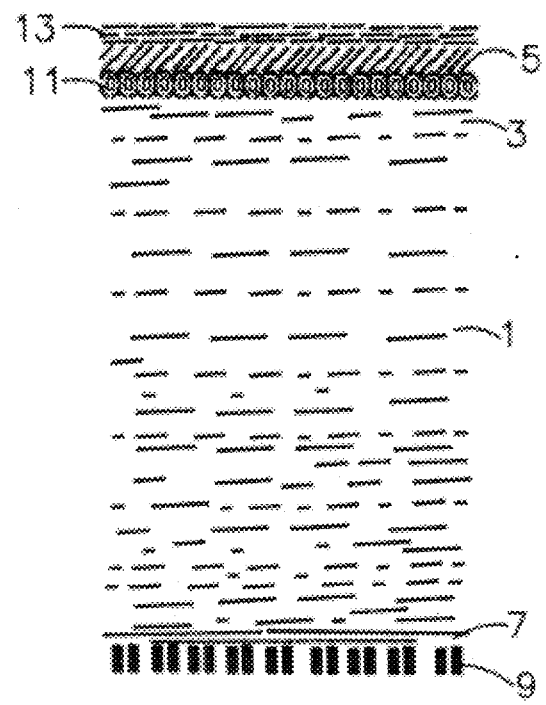
FIG. 1 illustrates a magnified meridional section through the human cornea.
Figure 8:
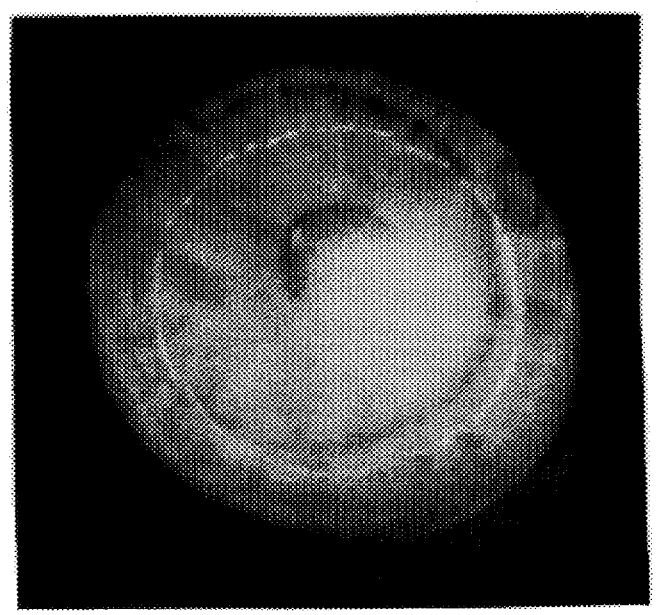
FIG. 8 is a photograph of a human cornea after its epithelium was removed by a rotating brush device in accordance with the invention.

The above tests on human subjects indicate an excellent quality of the denuded epithelium surface, as well as a dramatic decrease in the operation time itself. The mean time for epithelial removal with the rotating brush was about 3 seconds, with a range of about 2–5 seconds. This compares with the mean time of about 45 seconds (range: 30–120 seconds, based on inventor's own unpublished data) for epithelial removal with a beaver blade. Additionally, the rotating brush-abraded areas were round with regular and sharp edges, as clearly seen in FIG. 8. This is believed to aid in the healing process. In these studies, post PRK reepithelialization time using the rotating brush device never exceeded three days.

When the epithelial layer is abraded in a wet environment, further advantage is obtained. Continuous irrigation of the eye with normal saline during the procedure keeps the underlying stroma moist. In this manner, stromal desiccation is eliminated as a factor which could alter the stromal ablation rate from the rate used to calculate the proper number of laser pulses. Also, the saline lubricates the stroma making it less susceptible to damage from contact with the rotating relatively soft and pliable abrading surface. If a sponge material is used to provide the rotating abrading surface instead of a brush, the sponge should be moistened. In this case, it is unnecessary to separately irrigate the cornea during the removal procedure.

The results obtained with the inventive procedure and device are highly repeatable. With the exercise of routine surgical skill, precisely defined areas of the eye can be abraded without damage to the surrounding tissue. Since the abraded area can be easily controlled to correspond to the circular swath of the rotating abrading surface, the surgeon can precisely control the size of the abraded area by employing abrading heads of different sizes. In this manner, when performing a PRK or PTK procedure, it is possible to precisely limit the region in which the corneal epithelium is removed to that necessary for the subsequent photoablation.

The invention is not limited to the removal of a corneal epithelial layer. Rather, the inventive device can advantageously be utilized to selectively remove other soft eye tissues as well. The invention is particularly useful for selectively removing soft tissues that rest on somewhat firmer underlying tissues. One particular further application of the invention is described below.

After photoablation with an excimer laser, a so-called pseudo-membrane is created on the surface of the cornea as a result of left-over fiber of dehydrated collagen from the stroma. It is an extremely thin coat (some Å) created only because of the excimer laser. In normal conditions it does not exist on the cornea. Although conventionally this layer has been allowed to remain, recent tests indicate that, because the layer plays a role in stopping the flow of water and oxygen to the cornea during the first postoperative days, removal of the membrane is very important in the healing process of the cornea. The device of the present invention should be well suited for removal of this layer, since the relatively soft and pliable abrading surface provided by the rotating brush or sponge is rough and rigid enough to remove this soft thin layer without damaging the firmer underlying normal stromal layers.

The present invention has been described in terms of preferred embodiments thereof. Other embodiments and variations within the scope and spirit of the appended claims will, given the benefit of this disclosure, occur to those of ordinary skill in the art. For example, the invention is not limited to the brush and sponge embodiments described herein. Other devices such as pads of synthetic or natural fabric material may provide a relatively soft and pliable rotating surface capable of abrading away cornea/epithelium or a pseudo-membrane without damaging the underlying stroma.

I claim:

1. A procedure for removing a corneal epithelial layer from an eye, comprising:

exposing a corneal surface of the eye;

rotating a relatively soft and pliable abrading surface about a tool axis;

applying the rotating abrading surface to the corneal surface until the corneal epithelial layer has been abraded away, while leaving an underlying stromal layer wholly intact.

2. A procedure according to claim 1, wherein the relatively soft and pliable abrading surface is provided by bristle tips of a rotating brush.

3. A procedure according to claim 2, wherein the bristle tips are made of plastic.

4. A procedure according to claim 3, wherein the rotating brush has a circular shape centered about said tool axis.

5. A procedure according to claim 4, wherein said brush has a diameter of 4–10 mm.

6. A procedure according to claim 1, wherein the relatively soft and pliable abrading surface is rotated by a hand-held instrument while said abrading surface is manually applied to the cornea.

7. A procedure according to claim 1, further comprising the step of softening the corneal epithelium before the rotating abrading surface is applied to the exposed cornea.

8. A procedure according to claim 7, wherein the corneal epithelium is softened by applying to the eye drops containing an anesthetic.

9. A procedure according to claim 1, wherein the rotating abrading surface is applied to the exposed cornea for no more than 5 seconds.

10. A procedure according to claim 1, wherein the relatively soft and pliable abrading surface is rotated at 4000–6000 rpm.

11. A procedure according to claim 1, wherein the relatively soft and pliable abrading surface is provided by open cells of a sponge material.

12. A procedure according to claim 1, which includes a step of irrigating the eye with a liquid while the rotating abrading surface is applied to the exposed cornea.

13. A procedure according to claim 1, wherein said procedure is performed as part of a corneal laser ablation procedure including the subsequent step of ablating the underlying stromal layer in a controlled manner by impinging a laser beam thereon.

14. A procedure according to claim 13, wherein said corneal laser ablation procedure is PRK.

15. A procedure according to claim 13, wherein said corneal laser ablation procedure is PTK.

16. A procedure for removing soft tissue from an eye, comprising:
   exposing a soft tissue of the eye;
   rotating a relatively soft and pliable abrading surface provided by plastic bristle tips of a rotating brush about a tool axis; and
   applying the rotating abrading surface to the soft tissue until said soft tissue has been abraded away.

17. A procedure for removing soft tissue from an eye, comprising:
   exposing a soft tissue of the eye;
   rotating a relatively soft and pliable abrading surface on the end of a hand-held instrument while said abrading surface is manually applied to the eye; and
   applying the rotating abrading surface to the soft tissue until said soft tissue has been abraded away.

18. A procedure for removing soft tissue from any eye, comprising:
   exposing a soft tissue of the eye;
   rotating a relatively soft and pliable abrading surface provided by open cells of a sponge material about a tool axis; and
   applying the rotating abrading surface to the soft tissue until said soft tissue has been abraded away.

19. A procedure for removing soft tissue from an eye, comprising:
   exposing a soft tissue of the eye;
   rotating a relatively soft and pliable abrading surface about a tool axis; and
   applying the rotating abrading surface to the soft tissue until said soft tissue has been abraded away including removal of the soft tissue of the pseudo-membrane formed on a stromal layer by photoablation.

* * * * *